United States Patent [19]

Breuer et al.

[11] 4,052,554
[45] Oct. 4, 1977

[54] OXOPYRIDAZINYLTHIOMETHYL DERIVATIVES OF UREIDOCEPHALOSPORINS

[75] Inventors: Hermann Breuer; Uwe D. Treuner, both of Regensburg, Germany

[73] Assignee: E. R. Squibb & Sons, Inc., Princeton, N.J.

[21] Appl. No.: 714,890

[22] Filed: Aug. 16, 1976

Related U.S. Application Data

[62] Division of Ser. No. 611,041, Sept. 8, 1975, Pat. No. 3,996,218.

[51] Int. Cl.² .............. C07D 501/36; A61K 31/545
[52] U.S. Cl. .......................... 544/26; 544/21; 544/27; 424/246
[58] Field of Search ................... 260/243 C

[56] References Cited

U.S. PATENT DOCUMENTS

| | | | |
|---|---|---|---|
| 3,860,591 | 1/1975 | Breuer | 260/243 C |
| 3,892,737 | 7/1975 | Ochiai et al. | 260/243 C |
| 3,978,051 | 8/1976 | Dolfini | 260/243 C |

*Primary Examiner*—Nicholas S. Rizzo
*Attorney, Agent, or Firm*—Lawrence S. Levinson; Merle J. Smith; Stephen B. Davis

[57] ABSTRACT

Ureido cephalosporin derivatives of the formula

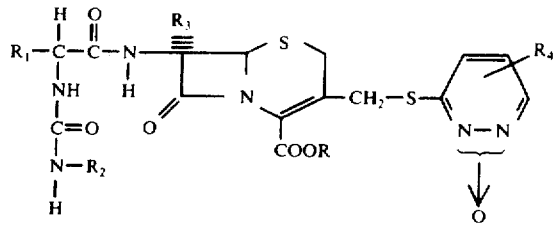

wherein R is hydrogen, lower alkyl, phenyl-lower alkyl, diphenyl-lower alkyl, tri(lower alkyl)silyl, trihaloethyl, a salt forming ion, or the group

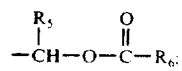

$R_1$ is hydrogen, lower alkyl, cycloalkyl, cycloalkenyl, cycloalkadienyl, phenyl, phenyl-lower alkyl, substituted phenyl or phenyl-lower alkyl, or certain heterocyclic groups; $R_2$ is hydrogen or lower alkyl; $R_3$ is hydrogen or methoxy; $R_4$ is hydrogen, halogen, lower alkyl, or lower alkoxy; $R_5$ is hydrogen or lower alkyl; $R_6$ is lower alkyl, phenyl, or phenyl-lower alkyl; are disclosed. These compounds are useful as anti-bacterial agents.

12 Claims, No Drawings

OXOPYRIDAZINYLTHIOMETHYL DERIVATIVES OF UREIDOCEPHALOSPORINS

This is a division, of application Ser. No. 611,041, filed Sept. 8, 1975, now U.S. Pat. No. 3,996,218.

BACKGROUND OF THE INVENTION

Cephalosporins having a ureido acyl side chain are disclosed in U.S. Pat. Nos. 3,673,183; 3,833,568; and 3,708,479. Cephalosporins having an (oxopyridazinyl)-thiomethyl group in the 3-position are disclosed in British Pat. No. 1,363,33. Cephalosporins having a methoxy group in the 7α-position are disclosed in various U.S. patents including U.S. Pat. Nos. 3,775,410; 3,780,031; 3,780,033; 3,780,034; 3,780,073, etc.

SUMMARY OF THE INVENTION

This invention relates to new oxopyridazinylthiomethyl derivatives of ureido-7α-methoxy or desmethoxy cephalosporins of the formula

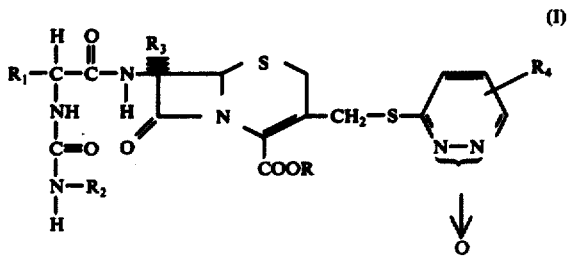

R represents hydrogen, lower alkyl, phenyl-lower alkyl, diphenyl-lower alkyl, tri(lower alkyl)silyl, trihaloethyl, a salt forming ion, or the group

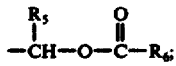

$R_1$ represents hydrogen, lower alkyl, cycloalkyl, cycloalkenyl, cycloalkadienyl, phenyl, phenyl-lower alkyl, substituted phenyl or phenyl-lower alkyl, or certain heterocyclics; $R_2$ represents hydrogen or loer alkyl; $R_3$ represents hydrogen or methoxy; $R_4$ represents hydrogen, halogen, lower alkyl of 1–4 carbons, or lower alkoxy of 1–4 carbons; $R_5$ represents hydrogen or lower alkyl; and $R_6$ represents lower alkyl, phenyl or phenyl-lower alkyl.

DETAILED DESCRIPTION OF THE INVENTION

The various groups represented by the symbols have the meaning defined below and these definitions are retained throughout this specification.

The lower alkyl groups referred to througout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e/.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

Cycloalkyl refers to groups having 3 to 7 carbons in the ring, i.e. cyclopropyl, cyclobutyl, cyclopentyl, cyclohexyl, and cycloheptyl. The terms cycloalkenyl and cycloalkadienyl also represent rings having 3 to 7 carbons with one or two double bonds, i.e. cyclobutenyl, cyclopentenyl, cyclohexenyl, cyclopentadienyl, cyclohexadienyl, etc. The double bond or bonds may be located at various positions, i.e. 1,4-cyclohexadienyl, etc.

The substituted phenyl and substituted phenyl-lower alkyl groups include one to three (preferably only one) simple substituents selected from halogen (preferably chlorine or bromine), lower alkyl, lower alkoxy, and hydroxy, e.g. 2-, 3-, or 4-chlorophenyl, 2-, 3-, or 4-bromophenyl, 3,5-dichlorophenyl, 2-methylphenyl, 4-ethoxyphenyl, 3,4,5-trimethoxyphenyl, 2-, 3- or 4-chlorobenzyl, 2-, 3-, or 4-methylphenethyl, etc.

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The halogens are the four common halogens, of which chlorine and bromine are preferred. in the case of the trihaloethyl group represented by R,2,2,2-trichloroethyl is preferred.

Trimethylsilyl is the preferred tri(lower alkyl)-silyl group.

The heterocyclics represented by $R_1$ are thienyl, furyl, pyrryl, pyridyl, thiazolyl, isothiazolyl, oxazolyl, isoxazolyl, thiadiazolyl, and tetrazolyl. They are attached at any available carbon atom as for example 2- or 3-thienyl, 2- or 3-furyl, 2- or 3-pyrryl, 2-, 3- or 4-pyridyl, 2-, 4- or 5-thiazolyl, 3-, 4- or 5-isothiazolyl, 2-, 4- or 5-oxazolyl, 3-, 4- or 5-isoxazolyl, 3- or 5-(1,2,4-thiadiazolyl), etc. Also included within the meaning of $R_1$ are such heterocyclics having a halogen (preferably Cl or Br) or a lower alkyl of 1-4 carbons (preferably methyl or ethyl) substituent, i.e. 5-(1-methyltetrazolyl), 2-(5-chlorothienyl)-2-(4-chloropyrryl), etc.

The structural formula for the pyridazine refers to the 1-oxide and to the 2-oxide.

The broken lines (━) between the cephalosporin nucleus and $R_3$ indicate that this substituent is in the α-configuration.

Preferred embodiments of this invention are as follows:

$R_1$ is phenyl, benzyl, phenethyl, substituted phenyl, benzyl, or phenethyl, cycloalkyl, cycloalkenyl and cycloalkadienyl of 5 to 7 carbons, thienyl, furyl, pyrryl, or pyridyl.

$R_2$ is hydrogen or lower alkyl of 1 to 4 carbons.

R is hydrogen, lower alkyl of 1 to 4 carbons, benzyl, phenethyl, diphenylmethyl, trimethylsilyl, 2,2,2-trichloroethyl, aluminum, alkaline earth metal, alkali metal, or

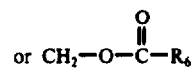

wherein $R_6$ is lower alkyl of 1 to 4 carbons, phenyl, benzyl or phenethyl.

$R_4$ is hydrogen.

The most preferred embodiments are:

$R_1$ is phenyl, substituted phenyl, 1,4-cyclohexadien-1-yl, 2-thienyl, 3-thienyl, or 3-pyridyl.

$R_2$ is hydrogen or methyl.

R is hydrogen, t-butyl, diphenylmethyl, or potassium.

Compounds of formula I are obtained by reacting an α-ureido compound of the formula $$R_1-CH-COOH \atop {| \atop NH-C-N-R_2 \atop \underset{O}{\|} \ \underset{H}{|}} \qquad (II)$$

with a 3-heterothio-7-amino substituted cephalosporin of the formula (III)

[structure of H₂N-cephalosporin with R₃, COOR, CH₂-S-pyridazine-R₄]

↓ wherein R is preferably diphenylmethyl or t-butyl or other ester protecting groups.

This reaction is carried out by converting the α-ureido compound of formula II to a mixed carbonic or other anhydride by treating a solution of the α-ureido compound in an organic solvent containing a tri(lower alkyl)amine with an anhydride forming agent, i.e. a lower alkyl chloroformate, an aryl chloroformate, or an acyl halide, at reduced temperatures of from about 0° C to about −20° C.

Alternatively, the α-ureido compound of formula II can be converted to an activated ester by reacting with a carboxyl group activating agent such as dicyclohexylcarbodiimide or bisimidazole carbonyl. In some cases the carboxyl group may be activated by conversion to an acid halide, e.g. the chloride, or to an azide.

The methods of preparing the α-ureido compounds of formula II are known to those skilled in the art and a number of such methods are discussed in U.S. Pat. Nos. 3,673,183 and 3,833,568 referred to above.

The compounds of formula I can also be prepared by acylating the compound of formula III with an acid chloride of formula $$R_1-CH-\underset{O}{\overset{\|}{C}}-Cl \atop {| \atop NH_2 \cdot HCl} \qquad (IV)$$

or an α-(substituted)amino acid of the formula $$R_1-CH-COOH \atop {| \atop NH-Y} \qquad (V)$$

wherein Y is a protecting group such as

[benzyl-CH₂-O-C(=O)- or]

[H₃CO-phenyl-CH₂-O-C(=O)- or]

$(CH_3)_3-C-O-\underset{O}{\overset{\|}{C}}-$ to yield after removal of the protecting group the intermediate of formula

[structure VI with R₁-CH-C(=O)-NH-cephalosporin-CH₂-O-C(=O)-CH₃, COOH, N-H, C=O, N-R₂, H]

The intermediate of formula VI is converted to the final products of formula I by treatment with an isocyanate of the formula $$R_2-N=C=O \qquad (VII)$$

or when $R_2$ is hydrogen an alkali or alkaline earth cyanate such as potassium cyanate in solution at a pH of from about 7 to about 8.

The final products of formula I wherein $R_3$ and R are hydrogen can also be prepared by reacting the compound of formula II with 7-ACA to yield the compound of formula VIII (VIII)

[structure of R₁-CH-NH-cephalosporin with N-H, C=O, N-R₂, H, CH₂-O-C(=O)-CH₃, COOH]

followed by treatment with the compound of the formula (IX)

[structure of R₄-pyridazine-SH, N—N]

↓ or a salt thereof, preferably an alkali metal salt like the potassium or sodium salt. This reaction is effected by bringing together the reactants in an aqueous solvent, preferably at a slightly alkaline pH with heating and under an inert atmosphere like nitrogen.

The starting material of formula IX is prepared as described in British Pat. No. 1,363,333.

Similarly, the final products of formula I can be prepared by reacting the compounds of formula IV or V with an ester of 7-ACA or 7α-methoxy-7ACA preferably in the presence of dicyclohexylcarbodiimide followed by treatment with an acid (HX), preferably trifluoroacetic acid in the presence of anisole, to yield the salt of formula

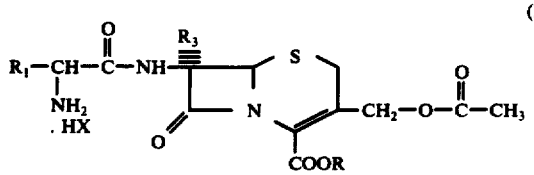

(X)

The salt of formula X is treated with the isocyanate of formula VII (or the alkali or alkaline earth cyanate where $R_2$ is hydrogen) followed by treatment with the compound of formula IX as described above to yield the final product of formula I.

The compounds of formula I wherein R is lower alkyl, phenyl-lower alkyl, substituted phenyl-lower alkyl, diphenyl-lower alkyl, or the acyloxymethyl group

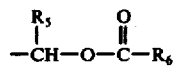

may be obtained by reacting the 3-heterothio-7-amino substituted cephalosporin of formula III or the 7-ACA or the 7α-methoxy-7ACA either before or after the acylation of the 7-amino substituent with one or two moles of a compound of the formula halo—R (XI)

or

R=N+=N- (XII)

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the 3-heterothio cephalosporanic acid moiety either before or after the acylation reaction.

The carboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom in the 7-position side chain. By selection of the appropriate starting material it is possible to obtain the compounds of formula I as a mixture of optically active isomers or isolated as a single isomer. The various isomers as well as their mixtures are within the scope of this invention. Where possible, it is generally preferred to obtain the D-isomer since that is the one which exhibits greater biological activity.

Illustrative process details are provided in the examples for the various reactions.

The compounds of formula I have a broad spectrum of antibacterial activity against both gram positive and gram negative organisms such as Staphylococus aureus, Salmonella schottmuelleri, Pseudomonas aeruginosa, Proteus vulgaris, Escherichia coli and Streptococcus pyogenes. They may be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of a compound of formula I or a physiologically accceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

The following examples are illustrative of the invention. All temperatures are on the centigrade scale.

EXAMPLE 1

7β-[[[(Aminocarbonyl)amino) (DL-2-thienyl)acetyl]amino]-3-[[(1-oxopyridazin-3-yl)thio]methyl]-8-oxo-5-thia-1-azabicyclo[4.2.0]oct-2-ene-2-carboxylic acid a. DL-α-ureido-2-thiopheneacetic acid 15.8 g. (0.1 mol.) of DL-2-thienylglycine are heated together with 8.2 g. (0.1 mol.) of potasssium cyanate in 100 ml. of water. After 30 minutes, the mixture is cooled and acidified with dilute hydrochloride acid. The precipitated product, D-β-ureido-2-thiopheneacetic acid, is filtered, washed with ice water and a small amount of ethanol. Recrystallization from methanol yields 17 g. of white crystals, of DL-α-ureido-2-thiopheneacetic acid; m.p. 183°-185°.

b. 3-[(Acetyloxy) methyl]-7β-[[[(aminocarbonyl-)amino](DL-2-thienyl)acetyl]amino]-8-oxo-5-thia-1-azabicyclo [4.2.0]-oct-2-ene-2-carboxylic acid 9.2 g. (50 mmol.) of DL-α-ureido-2-thiopheneacetic acid from part (a) are dissolved in 40 ml. of absolute dimethylformamide. 10.3 g. (50 mmol.) of dicyclohexylcarbodiimide dissolved in 1 ml. of methylene chloride are added dropwise at 0°. After stirring for ½ hour, a solution of 13.5 g. (50 mmol.) of 7-aminocephalosporanic acid and 10 g. (100 mmol.) of triethylamine is added. This mixture is stirred for 24 hours at 5°. After filtering, the filtrate is concentrated under vacuum, the oily residue is taken up in water, filtered and after treating with activated carbon at 5° it is layered over with ethyl acetate and acidifid with 2N hydrochloric acid. The ethyl acetate solution is washed with water, dried and concentrated. 8.1 g. of a viscid residue are obtained. The product, 3-[(acetyloxy)methyl]-7β-[[[(aminocarbonyl)-amino](DL-2-thienyl)acetyl]amino]-8-oxo-5-thia-1-azabicyclo-[4.2.0]oct-2-ene-2-carboxylic acid, is recrystallized twice from isopropanol; yield 2.1 g. The intermediate of part (b) can also be obtained by the following synthesis:

c. DL-[[[(1,2-Dimethylethoxy)carbonyl]amino]thien-2-yl]acetic acid 3.8 g. (25 mmol.) of DL-2-thienylglycine and 2 g. (50 mmol.) of magnesium oxide in 50 ml. of water/dioxane (1:1) are stirred for 1 hour at room temperature. 4.25 g. (28 mmol.) of t-butyloxycarbonylazide dissolved in 15 ml. of dioxane are added dropwise and the reaction mixture is stirred for 24 hours at 50°. After filtering, the filtrate is concentrated under vacuum, the oily residue is treated with ethyl acetate and then taken up with water. This is then acidified with citric acid while cooling with ice and the aqueous acid solution is extracted with ethyl acetate. The solvent is drawn off from the ethyl acetate solution to obtain 4 g. of white product, DL-[[[(1,1-dimethylethoxy)carbonyl]amino]thien-2-yl]acetic acid; m.p. 70°-72°.

d. 3-[(Acetyloxy)methyl]-7β-[[[(1,-dimethylethoxy)carbonyl]-amino](DL-2-thienyl)acetyl]amino]-8-oxo-5-thia-1-azabicyclo-[4.2.0]oct-2-ene-2-carboxylic acid, diphenylmethyl ester 5.4 g. (20 mmol.) of DL-[[[(1,1-dimethylethoxy)carbonyl]-amino]thien-2-yl]acetic acid from part (c) are dissolved in 50 ml. of tetrahydrofuran and 4.05 g. (20 mmol.) of dicyclohexylcarbodiimide are added at 0°. After stirring for 30 minutes, 8.8 g. (20 mmol.) of 7-aminocephalosporanic acid, diphenylmethyl ester are added dropwise. After 24 hours, the precipitated dicyclohexylurea is filtered off. After drawing off the solvent and recrystallizing the beige residue from methylene chloride/potassium ether 10.5 g. of the product, 3-[(acetyloxy)-methyl-7β-[[[(1,1-dimethylethoxy)carbonyl]amino]DL-2-thienyl)acetyl]amino]-8-oxo-5-thia-1-azabicyclo[4.2.0]oct-2-ene-2-carboxylic acid, diphenylmethyl ester, are obtained as a light beige powder; m.p. 78° (dec.).

e. 3-[(acetyloxy)methyl]-7β-[[[(aminocarbonyl)amino](DL-2-thienyl)acetyl]amino]-8-oxo-5-thia-1-azabicyclo[4.2.0]-oct-2-ene-2-carboxylic acid 5 g. of 3-[(acetyloxy)methyl]-7β-[[[(1,1-dimethylethoxy)carbonyl]amino](DL-2-thienyl)acetyl]amino]-8-oxo-5-thia-1-azabicyclo[4.2.0]-oct-2-ene-2-carboxylic acid, diphenylmethyl ester from part (d) are stirred for 15 minutes in a mixture of 20 ml. of trifluoroacetic acid and 3 ml. of anisole at 5°. After evaporating the trifluoroacetic acid under vacuum and washing the residue with ether, 2.3 g. of 3-[(acetyloxy)-methyl]-7β-[[(2-amino-DL-2-thienyl)acetyl]amino]-8-oxo-5-thia-1-azabicyclo[4.2.0]oct-2-ene-2-carboxylic acid, trifluoroacetic acid salt are obtained. This product is dissolved in water and the solution is adjusted to pH 8 with sodium hydroxide. It is then quickly heated to 80° and 0.4 g. of potassium cyanate dissolved in 2 ml. of water are added. After stirring for 1 minute, the reaction mixture is quickly cooled, layered over with ethyl acetate and acidified to pH 3.5 with 2N hydrochloric acid. This is extracted with 5 × 100 ml. of ethyl acetate. The combined ethyl acetate extracts are dried, concentrated to about ¼ the volume, treated with activated carbon and the product, 3-[(acetyloxy)methyl]-7β-[[[(aminocarbonyl)-amino](DL-2-thienyl)acetyl]amino]-8-oxo-5-thia-1-azabicyclo-[4.2.0]oct-2-ene-2-carboxylic acid, is precipitated with petroleum ether. The product is crystallized from isopropanol as light being crystals; m.p. 145° (dec.).

f. 7β-[[[(Aminocarbonxyl)amino](DL-2-thienyl)acetyl]-amino]-3-[[(1-oxopyridazin-3-yl)thio]methyl]-8-oxo-5-thia-1-azabicyclo-[4.2.0]-oct-2-ene-2-carboxylic acid The 3-[(acetyloxy)methyl]-7β-[[[(aminocarbonyl)amino]-(DL-2-thienyl)acetyl]amino]-8-oxo-5-thia-1-azabicyclo[4.2.0]-oct-2-ene-2-carboxylic acid from part (b) or (e) is dissolved in a mixture of acetone/water (1:1) with the aid of 5N sodium hydroxide. 1-Oxopyridazine-3-thiol, sodium salt is added under nitrogen and the solution is heated for several hours at 60°. The solution is diluted with 150 ml. of water and acidified to pH 5 with 2N hydrochloric acid while cooling. A precipitate forms which is filtered under suction to yield 7β-[[[(aminocarbonyl)amino](DL-2-thienyl)acetyl]amino]-3-[[(1-oxopyridazin-3-yl)thio]methyl]-8-oxo-5-thia-1-azabicyclo[4.2.0]oct-2-ene-2-carboxylic acid.

EXAMPLE 2

7β-[[[(Aminocarbonyl)amino](DL-2-thienyl)acetyl]-amino]-3-[[(1-oxypyridazin-3-yl)thio]methyl]-8-oxo-5-thia-1-azabicyclo-[4.2.0]-oct-2-ene-2-carboxylic acid, potassium salt An equimolar solution of the final product from example 1 and potassium bicarbonate is freeze-dried to yield the titled compound as a powder.

EXAMPLE 3

7β-[[[(Aminocarbonyl)amino](DL-3-thienyl)acetyl]-amino]-3-[[(1-oxopyridazin-3-yl)thio]methyl]-8-oxo-5-thia-1-azabicyclo-[4.2.0]oct-2-ene-2-carboxylic acid a. DL-α-Bromo-3-thiopheneacetic acid 3-thienylbromide is treated with butyl lithium and chloral to obtain 3-[(1-hydroxy-2-trichloro)ethyl]thiophene which is then treated with sodium methoxide to obtain α-methoxy-3-thienylacetic acid [Gronowitz et al., Ark. Chemi., 17, 561 (1961)].

150 ml. of 30% hydrogen bromide in acetic acid is added to a solution of 16 g. (100 mmol.) of (α-methoxy-3-thienyl)acetic acid in 50 ml. of glacial acetic acid. The mixture is left to stand at room temperature for 24 hours and then poured into ice water. The solution is extracted three times with 60 ml. of ether. The ether phase is washed with water, dried over magnesium sulfate and evaporated. The residue, 18 g. of crude DL-α-bromo-3-thiopheneacetic acid are recrystallized from cyclohexane; yield 14 g.; m.p. 80°-82°.

b. DL-α-Azido-3-thiopheneacetic acid 4 g. (62 mmol.) of sodium azide and 3.5 g. (33 mmol.) of sodium carbonate are added to a solution of 12 g. (54 mmol.) of DL-α-bromo-3-thiopheneacetic acid in 75 ml. of acetone (96%). The mixture is stirred at room temperature for 12 hours in darkness and after this time the solvent is evaporated and the residue is dissolved in 75 ml. of water. 50 ml. of ether is added, the water phase is acidified with 2N sulfuric acid and extracted quickly twice more with 50 ml. of ether. After washing with water and drying over sodium sulfate, the combined ether phases are evaporated. Crystallization of the residue from cyclohexane yields 7.4 g. of white crystalline DL-α-azido-3-thiopheneacetic acid; m.p. 58°-59°.

c. DL-α-Amino-3-thiopheneacetic acid 0.3 g. of palladium/barium sulfate catalyst are added to a solution of 6 g. of DL-β-azido-3-thiopheneacetic acid in 40 ml. of ethanol and 40 ml. of 0.5N hydrochloric acid. Hydrogenation takes place at about 60 psig. after 2 hours. After filtration, the volume is concentrated to about 30 ml. When the pH is brought to 6.5 with ammonia, the amino acid separates as a white powder. After washing with ethanol/water and drying, 3.5 g. of the product, DL-α-amino-3-thiopheneacetic acid, are obtained; m.p. 283°-285°.

d. DL-α-[[[(4-Methoxyphenyl)methoxy]carbonyl]amino]-3-thiopheneacetic acid 1.9 g. (12.5 mmol.) of DL-α-amino-3-thiopheneacetic acid and 1 g. of magnesium oxide are stirred in 25 ml. of water and 25 ml. of dioxane. After stirring for 1 hour, 3.0 g. (15 mmol.) of [(p-methoxybenzyl)oxy]carbonylazide are added. Stirring is continued for 24 hours. The mixture is filtered and extracted with 2 ml. of ether. 50 ml. of ethyl acetate and 20 g. of Dowex 50 (H+ form) are added to the filtrate and the mixture is stirred well for two hours. The ethyl acetate phase is separated, washed with 50 ml. of water, dried over sodium sulfate and evaporated. The oily residue crystallizes after the addition of pentane to yield 3.4 g. of white crystalline DL-α-[[[(4-methoxyphenyl)methoxy]carbonyl]amino]-3-thiopheneacetic acid; m.p. 118° (dec.).

e. 3-[(Acetyloxy)methyl]-7β-[[[[[(4-methoxyphenyl)methoxy]carbonyl]amino]DL-3-thienyl)acetyl]amino]-8-oxo-5-thia-1-azabicyclo[4.2.0]oct-2-ene-2-carboxylic acid 5 g. of the product from part (d), 1.5 g. of triethylamine and 1.8 g. of chloroformic acid ethyl ester in 50 ml. of tetrahydrofuran are converted to the mixed anhydride. The mixed anhydride is reacted with a solution of 4 g. of 7-aminocephalosporanic acid and 2.5 g. of triethylamine in methylene chloride for 12 hours. The solvent is then removed from the solution and the partially solid residue is dissolved with water and a small amount of sodium carbonate and extracted with 50 ml. of ethyl acetate. The aqueous phase is cooled, acidified to pH 2.5 with 2N hydrochloric acid and extracted with ethyl acetate. The organic phase is treated with activated carbon and concentrated to obtain 3.7 g. of light beige product, 3-[(acetyloxy)methyl]-7β-[[[[[(4-methoxyphenyl)methoxy]carbonyl]-amino](DL-3-thienyl)acetyl]amino]-8-oxo-5-thia-1-azabicyclo[4.2.0]oct-2-ene-2-carboxylic acid; m.p. 113° (dec.), which is recrystallized from methylene chloride/petroleum ether.

f. 3-[(Acetyloxy)methyl]-7β-[[[(aminocarbonyl)amino](DL-3-thienyl)-acetyl]amino]-8-oxo-5-thia-1-azabicyclo[4.2.0]oct-2-ene-2-carboxylic acid The product from part (e) is stirred with 15 ml. of trifluoroacetic acid and then reacted with potassium cyanate as described in example 1(e) to yield the titled compound.

g. 7β-[[[(Aminocarbonyl)amino](DL-3-thienyl)acetyl]amino]-3-[[(1-oxopyridazin-3-yl)thio]methyl]-8-oxo-5-thia-1-azabicyclo[4.2.0]oct-2-ene-2-carboxylic acid The 3-[(acetyloxy)methyl]-7β-[[[(aminocarbonyl)amino]-(DL-3-thienyl)acetyl]amino]-8-oxo-5-thia-1-azabicyclo[4.2.0]oct-2-ene-2-carboxylic acid from part (f) is treated with 1-oxopyridazine-3-thiol according to the procedure of example 1(f) to yield the titled compound.

EXAMPLE 4

7β-[[[(Aminocarbonyl)amino](D-2-thienyl)acetyl[-amino]-7α-methoxy-3-[[(1-oxopyridazin-3-yl)thio]methyl]-8-oxo-5-thia-1-azabicyclo[4.2.0]oct-2-ene-2-carboxylic acid a. D-α-[[[(4-Methoxyphenyl)methoxy]carbonyl]-amino]-2-thiophene-acetic acid 15.7 g. of D-(2-thienyl)glycine (m.p. 218°-219°, produced from the racemate with D-camphor-10-sulfonic acid) and 8 g. of magnesium oxide are suspended in 200 ml. of water. To this suspension is added a solution of 22.8 g. of (p-methoxyphenyl)methoxycarbonylazide in 200 ml. of dioxane and this mixture is stirred for 3 days at room temperature. The mixture is filtered, the filtrate is extracted once with ether, the aqueous phase is layered over with ethyl acetate, cooled to about 10° and acidified to pH 2 with dilute hydrochloric acid. The aqueous phase is once more extracted with ethyl acetate, the combined extracts are washed once with water, dried with magnesium sulfate and concentrated. The residue crystallizes upon trituration with petroluem ether. The crude product D-α-[[[(4-methoxyphenyl)methoxy]carbonyl]amino]-2-thiopheneacetic acid, is recrystallizeed from ethyl acetate/petroleum ether, yield 25.2 g., m.p. 65°-67°.

b. 3-[(Acetyloxy)methyl]-7β-[[[[[(4-methoxyphenyl)-methoxy]-carbonyl]amino](D-2-thienyl)acetyl]-amino]-7α-methoxy-8 -oxo-5-thia-1-azabicyclo[4.2.0]-oct-2-ene-2-carboxylic acid, diphenylmethyl ester 3.2 g. (0.01 mol.) of the product from part (a) is brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 4.7 g. (0.01 mol.) of 7β-amino-7α-methoxy cephalosporanic acid diphenylmethyl ester and 3.1 ml. of triethylamine in 40 ml. of methylene chloride. The mixture is stirred for 1 hour at −5° and 1 hour at 5°. This mixture is then evaporated to dryness in a rotary evaporator and the solid residue is triturated with ether and filtered under suction to yield the titled compound.

c. 3-[(Acetyloxy)methyl]-7β-[[(α-amino-D-2-thienyl)acetyl]amino]-7α-methoxy-8-oxo-5-thia-1-azabicyclo[4.2.0]oct-2-ene-2-carboxylic acid 2.0 g. of the product from part (b) are added at −5° to a mixture of 10 ml. of trifluoroacetic acid and 4 ml. of anisole. The mixture is stirred for 15 minutes and is then concentrated in a rotary evaporator. The residue is treated with ether and filtered under suction. The crude 3-[(acetyloxy)methyl]-7β-[[(2-amino-D-2-thienyl)acetyl]amino]-7α-methoxy-8-oxo-5-thia-1-azabicyclo[4.2.0]oct-2-ene-2-carboxylic acid, trifluoroacetic acid salt is dissolved in 50 ml. of water and 20 ml. of a solution of the acetate form of the ion exchange resin Amberlite LA 1 in isobutylmethylketone are added. The mixture is stirred for 2 hours at room temperature. The layers are separated, the aqueous phase is washed several times with ether and freeze-dried to yield 3-[(acetyloxy)methyl]-7β-[[(α-amino-D-2-thienyl)acetyl]-amino]-7α-methoxy-8-oxo-5-thia-1-azabicyclo[4.2.0]-oct-2-ene-2-carboxylic acid.

d. 3-[(Acetyloxy)methyl]-7β-[[[(aminocarbonyl)amino] (D-2-thienyl)-acetyl]amino]-7α-methoxy-8-oxo-5-thia-1-azabicyclo[4.2.0]oct-2-ene-2-carboxylic acid A mixture of 1 g. of the product from part (c) and 0.194 g. of potassium cyanate in 7.5 ml. of water are quickly heated in a preheated bath at 80°. The mixture is then immediately cooled to room temperature and permitted to stand overnight. The reaction mixture is concentrated to about 4 ml. and the pH is adjusted to 1.5 with 2N hydrochloric acid. The precipitate is filtered under suction to obtain 3-[(acetyloxy)methyl]-7β-[[[(aminocarbonyl)amino] (D-2-thienyl)acetyl]amino]-

7α-methoxy-8-oxo-5-thia-1-azabicyclo[4.2.0]oct-2-ene-2-carboxylic acid.

e. 7β-[[[(Aminocarbonyl)amino](D-2-thienyl)acetyl]amino]-7α-methoxy-3-[[(1-oxopyridazin-3-yl)thio]methyl]-8-oxo-5-thia-1-azabicyclo[4.2.0]oct-2-ene-2-carboxylic acid 0.01 moles of the product from part (d) and 0.011 moles of 1-oxopyridazine-3-thiol are heated in an aqueous acetone solution according to the procedure of example 1 (f) to yield 7β-[[[(aminocarbonyl)amino](D-2-thienyl)acetyl]amino]-7α-methoxy-3-[[[(1-oxopyridazin-3-yl)thio]methyl]-8-oxo-5-thia-1-azabicyclo[4.2.0]-oct-2-ene-2-carboxylic acid.

EXAMPLES 5-11

Following the procedure of example 1 but substituting for the 1-oxopyridazine-3-thiol one of the following:

2-oxopyridazine-3-thiol
4-methyl-1-oxopyridazine-3-thiol
6-ethoxy-1-oxopyridazine-3-thiol
5-t-butyl-2-oxopyridazine-3-thiol
6-chloro-1-oxopyridazine-3-thiol
4-bromo-2-oxopyridazine-3-thiol
6-methoxy-2-oxopyridazine-3-thiol obtains:

7β-[[[(aminocarbonyl)amino](DL-2-thienyl)acetyl]amino]-3-[[[(2-oxopyridazin-3-yl)thio]methyl]-8-oxo-5-thia-1-azabicyclo-[4.2.0]oct-2-ene-2-carboxylic acid, 7β-[[[(aminocarbonyl)amino (DL-2-thienyl)acetyl]amino]-3-[[(4-methyl-1-oxopyridazin-3-yl)thio]methyl]-8-oxo-5-thia-1-azabicyclo[4.2.0]oct-2-ene-2-carboxylic acid, 7β-[[[(aminocarbonyl)amino](DL-2-thienyl)acetyl]amino]-3-[[(6-ethoxy-1-oxopyridazin-3-yl)thio]methyl]-8-oxo-5-thia-1-azabicyclo[4.2.0]oct-2-ene-2-carboxylic acid, 7β-[[[(aminocarbonyl)amino](DL-2-thienyl)acetyl]amino]-3-[[(5-t-butyl-2-oxopyridazin-3-yl)thio]methyl]-8-oxo-5-thia-1-azabicyclo[4.2.0]oct-2-ene-2-carboxylic acid, 7β-[[[(aminocarbonyl)amino](DL-2-thienyl)acetyl]amino]-3-[[(6-chloro-1-oxopyridazine-3-yl)thio]methyl]-8-oxo-5-thia-1-azabicyclo[4.2.0]oct-2-ene-2carboxylic acid, 7β-[[[(aminocarbonyl)amino](DL-2-thienyl)acetyl]amino]-3-[[(4-bromo-2-oxopyridazin-3-yl)thio]methyl]-8-oxo-5-thia-1-azabicyclo[4.2.0]oct-2-ene-2-carboxylic acid, and 7β-[[[(aminocarbonyl)amino](DL-2-thienyl)acetyl]amino]-3-[[(6-methoxy-2-oxopyridazin-3-yl)thio]methyl]-8-oxo-5-thia-1-azabicyclo[4.2.0]oct-2-ene-2-carboxylic acid, respectively.

EXAMPLES 12-18

Following the procedure of example 4 but substituting for the 1-oxopyridazine-3-thiol the pyridazines of examples 5-11 one obtains the following compounds:

7β-[[[(aminocarbonyl)amino](D-2-thienyl)acetyl]amino]-7α-methoxy-3-[[(2-oxopyridazin-3-yl )thio]methyl]-8-oxo-5-thia-1-azabicyclo[4.2.0]oct-2-ene-2-carboxylic acid, 7β-[[[(aminocarbonyl)amino](D-2-thienyl)acetyl]amino]-7α-methoxy-3-[[(4-methyl-1-oxopyridazin-3-yl)thio]methyl]-8-oxo-5-thia-1-azabicyclo[4.2.0]oct-2-ene-2-carboxylic acid, 7β-[[[(aminocarbonyl)amino](D-2-thienyl)acetyl]amino]-7α-methoxy-3-[[(6-ethoxy-1-oxopyridazin-3-yl)thio]methyl]-8-oxo-5-thia-1-azabicyclo[4.2.0]oct-2-ene-2-carboxylic acid, 7β-[[[(aminocarbonyl)amino](D-2-thienyl)acetyl]amino]-7α-methoxy-3-[[(5-t-butyl-2-oxopyridazin-3-yl)thio]methyl]-8-oxo-5-thia-1-azabicyclo[4.2.0]oct-2-ene-2-carboxylic acid, 7β-[[[(aminocarbonyl)amino](D-2-thienyl)acetyl]amino]-7α-methoxy-3-[[(6-chloro-1-oxopyridazin-3-yl)thio]methyl]-8-oxo-5-thia-1-azabicyclo[4.2.0]oct-2-carboxylic acid, 7β-[[[(aminocarbonyl)amino](D-2-thienyl)acetyl]amino]-7α-methoxy-3-[[(4-bromo-2-oxopyridazin-3-yl)thio]methyl]-8-oxo-5-thia-1-azabicyclo[4.2.0]oct-2-ene-2-carboxylic acid, and 7β-[[[(aminocarbonyl)amino](D-2-thienyl)acetyl]amino]-7α-methoxy-3-[[(6-methoxy-2-oxopyridazin-3-yl)thio]methyl]-8oxo-5-thia-1-azabicyclo[4.2.0]oct-2-ene-2-carboxylic acid, respectively.

EXAMPLES 19-72

Following the procedure of either example 1 or 4 but employing the α-amino acid shown in Col. I one obtains the compound shown in Col. II (procedure of example 1) or Col. III (procedure of example 4).

| Ex. | $R_1$ |
|---|---|
| 19 | H |
| 20 | $CH_3$ |
| 21 | $C_2H_5$ |
| 22 | $t-C_4H_9$ |
| 23 | $n-C_5H_{11}$ |
| 24 | cyclopropyl-CH- |
| 25 | cyclobutyl- |
| 26 | cyclopentyl- |
| 27 | cyclohexyl- |

Col. I: $R_1$—CH(NH$_2$)—COOH

Col. II and Col. III: cephalosporin structures with $R_1$—CH(NH—C(=O)—NH$_2$)—C(=O)—NH— linked to the β-lactam bearing either H (Col. II) or OCH$_3$ (Col. III) at the 7α-position, and —CH$_2$—S-(1-oxopyridazin-3-yl) at the 3-position.

4,052,554
-continued
Col. I
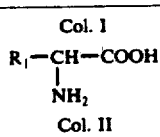
Col. II
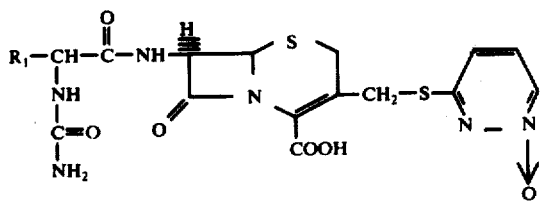
Col. III
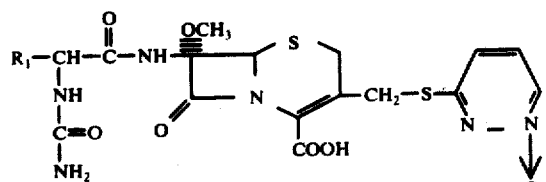
| Ex. | R₁ |
|---|---|
| 28 | 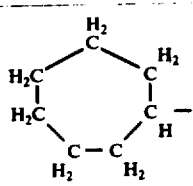 |
| 29 |  |
| 30 | 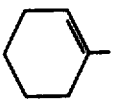 |
| 31 | 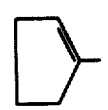 |
| 32 |  |
| 33 |  |
| 34 |  |
| 35 | 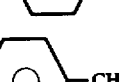 |
| 36 | 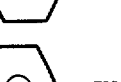 |
| 37 | |
-continued
Col. I
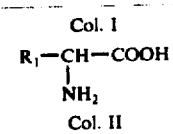
Col. II
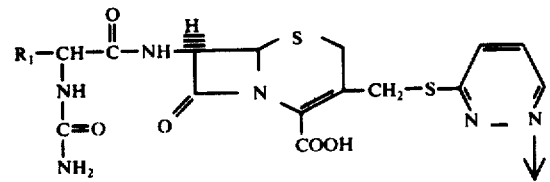
Col. III
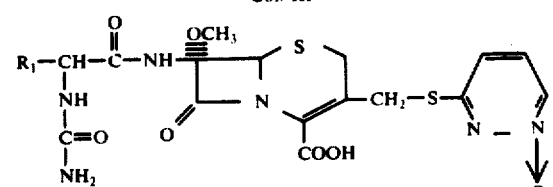
| Ex. | R₁ |
|---|---|
| 38 | 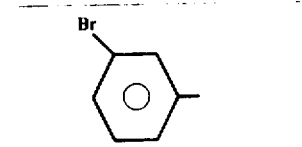 |
| 39 |  |
| 40 | 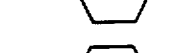 |
| 41 |  |
| 42 | 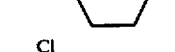 |
| 43 | 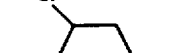 |
| 44 |  |
| 45 | 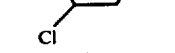 |
| 46 | 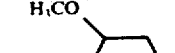 |

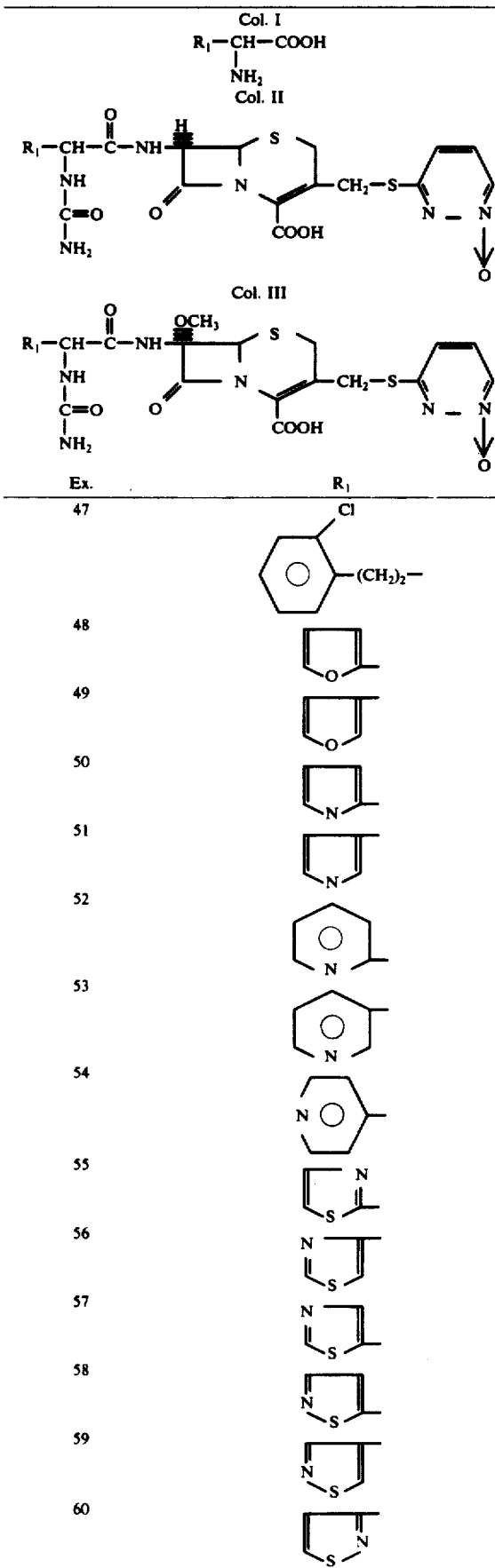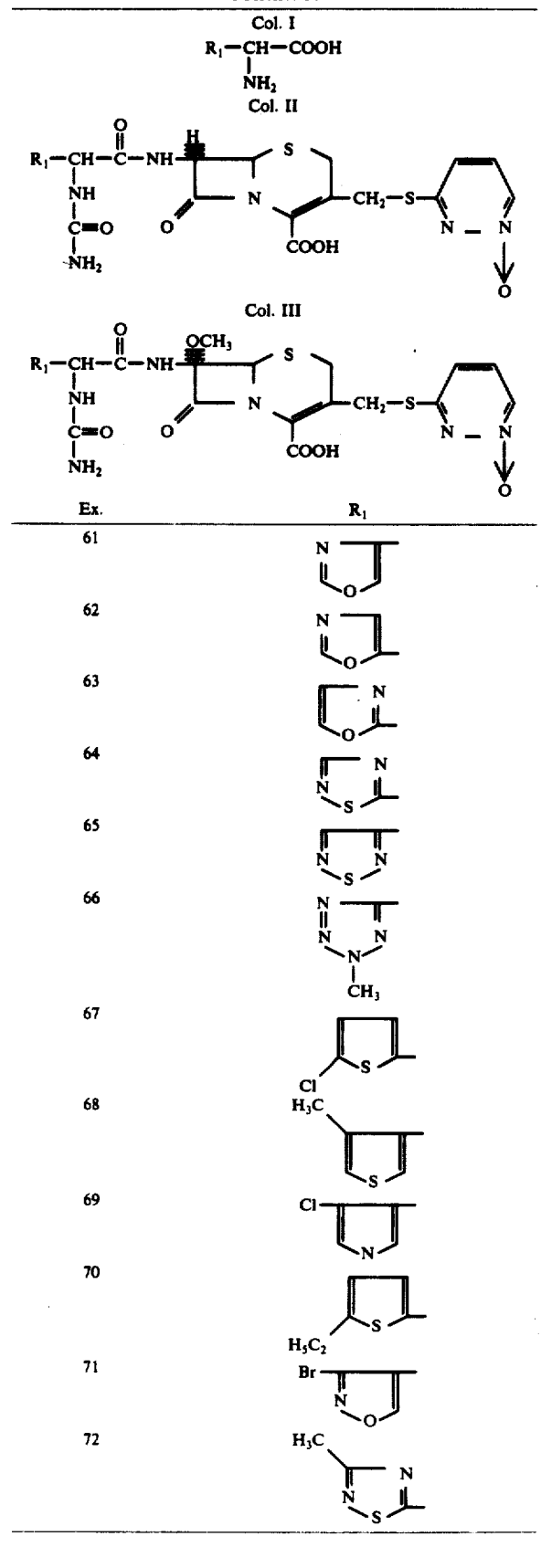

EXAMPLE 73

7β-[[[(Methylaminocarbonyl)amino](DL-2-thienyl-
)acetyl]amino]-3-[[(1-oxopyridazin-3-yl)thio]methyl]-8-
oxo-5-thia-1-azabicyclo[4.2.0]oct-2-ene-2-carboxylic
acid a. 3-[(Acetyloxy)methyl]-7β-[[[(methylaminocarbonyl-
)amino](DL-2-thienyl)acetyl]-8-oxo-5-thia-1-azabicy-
clo[4.2.0]oct-2-ene-2-carboxylic acid 1.5 g. of 3-[(acetyloxy)methyl]-7β-[[(2-amino-DL-2-
thienyl)acetyl]amino]-8-oxo-5-thia-1-azabicyclo[4.2.0]-
oct-2-ene-2-carboxylic acid, trifluoroacetic acid salt
from example 1(e) and 1.01 ml. of triethylamine are
dissolved at 0°–5° in 20 ml. of anhydrous methylene
chloride. To the clear solution is added 2.49 g. of a 10%
solution of methylisocyanate in methylene chloride.
This mixture is stirred for 2 hours at 0°–5° and then
concentrated. The residue is taken up in a little water,
shaken with ether, filtered and acidified with 2N hydro-
chloric acid to yield 3-[(acetyloxy)methyl]-7β-[[[(me-
thylaminocarbonyl)-amino](DL-2-thienyl)acetyl]-
amino]-8-oxo-5-thia-1-azabicyclo[4.2.0]oct-2-ene-2-car-
boxylic acid.

b. 7β-[[[(Methylaminocarbonyl)amino](DL-2-thienyl-
)acetyl]amino]-3-[[(1-oxopyridazin-3-yl)thio]methyl]-
8-oxo-5-thia-1-azabicyclo[4.2.0]oct-2-ene-2-carboxy-
lic acid 0.01 mol. of the product from part (a) and 0.011 mol.
of 1-oxopyridazine-3-thiol are reacted according to the
procedure of example 1(f) to yield 7β-[[[(me-
thylaminocarbonyl)amino](DL-2-thienyl)acetyl]-
amino]-3-[[[(1-oxopyridazine-3-yl)thio]methyl]-8-oxo-5-
thia-1-azabicyclo[4.2.0]oct-2-ene-2-carboxylic acid.

EXAMPLES 74–80

Following the procedure of example 73 but substitut-
ing for the methylisocyanate one of the following:
ethylisocyanate
n-propylisocyanate
i-propylisocyanate
n-butylisocyanate
i-butylisocyanate
t-butylisocyanate
n-pentylisocyanate
one obtains:
7β-[[[(ethylaminocarbonyl)amino](DL-2-thienyl-
)acetyl]amino]-3-[[(1-oxopyridazin-3-yl)thio]methyl]-8-
oxo-5-thia-1-azabicyclo-[4.2.0]oct-2-ene-2-carboxylic
acid;
7β-[[[(n-propylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid;
7β-[[[(i-propylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid;
7β-[[[(n-butylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid;
7β-[[[(i-butylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid;
7β-[[[(t-butylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid; and
7β-[[[(n-pentylaminocarbonyl)amino](DL-2-thienyl-
)acetyl]-amino]-3-[[(1-oxopyridazin-3-yl)thio]methyl]-
8-oxo-5-thia-1-azabicyclo[4.2.0]oct-2-ene-2-carboxylic
acid; respectively.

Similarly, by employing the methylisocyanate from
example 73 or the alkylisocyanates of examples 74–80 in
the procedure of examples 3, 5 to 11, and 19 to 72, other
compounds within the scope of this invention are ob-
tained.

EXAMPLE 81

7β-[[[(Methylaminocarbonyl)amino](D-2-thienyl-
)acetyl]amino]-7α-methoxy-3-[[(1-oxopyridazin-3-
yl)thio]methyl]-8-oxo-5-thia-1-azabicyclo[4.2.0]oct-
2-ene-2-carboxylic acid a. 3-[(Acetyloxy)methyl]-7β-[[[(methylaminocarbonyl-
)amino ]-(D-2-thienyl)acetyl]amino]-7α-methoxy-8-
oxo-5thia-1-azabicyclo[4.2.0]oct-2-ene-2-carboxylic
acid 1.5 g. of 3-[(acetyloxy)methyl]-7β-[[(2-amino-D-2-
thienyl)acetyl]amino]-7α-methoxy-8-oxo-5-thia-1-
azabicyclo-[4.2.0]oct-2-ene-2-carboxylic acid, trifluoro-
acetic acid salt from example 4(c) and 1.01 ml. of trieth-
ylamine are dissolved at 0°–5° in 20 ml. of anhydrous
methylene chloride. To the clear solution is added 2.49
g. of a 10% solution of methylisocyanate in methylene
chloride. This mixture is stirred for 2 hours at 0°–5° and
then concentrated. The residue is taken up in a little
water, shaken with ether, filtered and acidified with 2N
hydrochloric acid to yield 3-[(acetyloxy)-methyl]-7β-
[[[(methylaminocarbonyl)amino](D-2-thienyl)acetyl]-
amino]-7α-methoxy-8-oxo-5-thia-1-azabicyclo[4.2.0]-
oct-2-ene-2-carboxylic acid.

b. 7β-[[[(Methylaminocarbonyl)amino](D-2-thienyl-
)acetyl]amino]-7α-methoxy-3-[[(1-oxopyridazin-3-
yl)thio]methyl]-8-oxo-5-thia-1-azabicyclo[4.2.0]oct-
2-ene-2-carboxylic acid 0.01 mol. of the product from part (a) and 0.011 mol.
of 1-oxopyradazine-3-thiol are reacted according to the
procedure of example 1(f) to yield 7β-[[[(met-
hylaminocarbonyl)-amino](D-2-thienyl)acetyl]amino]-
7α-methoxy-3-[[(1-oxopyradazin-3-yl)thio]methyl]-8-
oxo-5-thia-1-azabicyclo[4.2.0]oct-2-ene-2-carboxylic
acid.

EXAMPLES 82–88

Following the procedure of examples 81 but substitut-
ing for the methylisocyanate one of the following:
ethylisocyanate
n-propylisocyanate
i-propylisocyanate
n-butylisocyanate
i-butylisocyanate
t-butylisocyanate
n-pentylisocyanate
one obtains:
7β-[[[(ethylaminocarbonyl)amino](D-2-thienyl-
)acetyl]-amino]-7α-methoxy-3-[[(1-oxopyridazin-3-
yl)thio]methyl]-8-oxo-5-thia-1-azabicyclo[4.2.0]oct-
2-ene-2-carboxylic acid;
7β-[[[(n-propylaminocarbonyl)amino](D-2-thienyl-
)acetyl]-amino]-7α-methoxy-3-[[(1-oxopyradazin-3-
yl)thio]methyl]-8-oxo-5-thia-1-azabicyclo[4.2.0]oct-
2-ene-2-carboxylic acid;

7β-[[[(i-propylaminocarbonyl)amino](D-2-thienyl-
)acetyl]-amino]-7α-methoxy-3-[[(1-oxopyradazin-3-
yl)thio]methyl]-8-oxo-5-thia-1-azabicyclo[4.2.0]oct-
2-ene-2-carboxylic acid;

7β-[[[(n-butylaminocarbonyl)amino](D-2-thienyl-
)acetyl]-amino]-7α-methoxy-3-[[(1-oxopyridazin-3-
yl)thio]methyl]-8-oxo-5-thia-1-azabicyclo[4.2.0]oct-
2-ene-2-carboxylic acid;

7β-[[[(i-butylaminocarbonyl)amino](D-2-thienyl-
)acetyl]-amino]-7α-methoxy-3-[[(1-oxopyridazin-3-
yl)thio]methyl]-8-oxo-5-thia-1-azabicyclo[4.2.0]oct-
2-ene-2-carboxylic acid;

7β-[[[(t-butylaminocarbonyl)amino](D-2-thienyl-
)acetyl]-amino]-7α-methoxy-3-[[(1-oxopyridazin-3-
yl)thio]methyl]-8-oxo-5-thia-1-azabicyclo[4.2.0]oct-
2-ene-2-carboxylic acid; and 7β-[[[(n-pentylaminocarbonyl)amino](D-2-thienyl-
)acetyl]-amino]-7α-methoxy-3-[[(1-oxopyridazin-3-
yl)thio]methyl]-8-oxo-5-thia-1-azabicyclo[4.2.0]oct-
2-ene-2-carboxylic acid respectively.

Similarly, by employing the methylisocyanate from example 81 or the alkylisocyanates of examples 82-88 in the procedure of examples 12 to 18 other compounds within the scope of this invention are obtained.

EXAMPLES 89-106

Following the procedure of example 1 but employing the appropriate ester of 7-aminocephalosporanic acid or by reacting the final product of example 1, esters and salts of the following formula are obtained

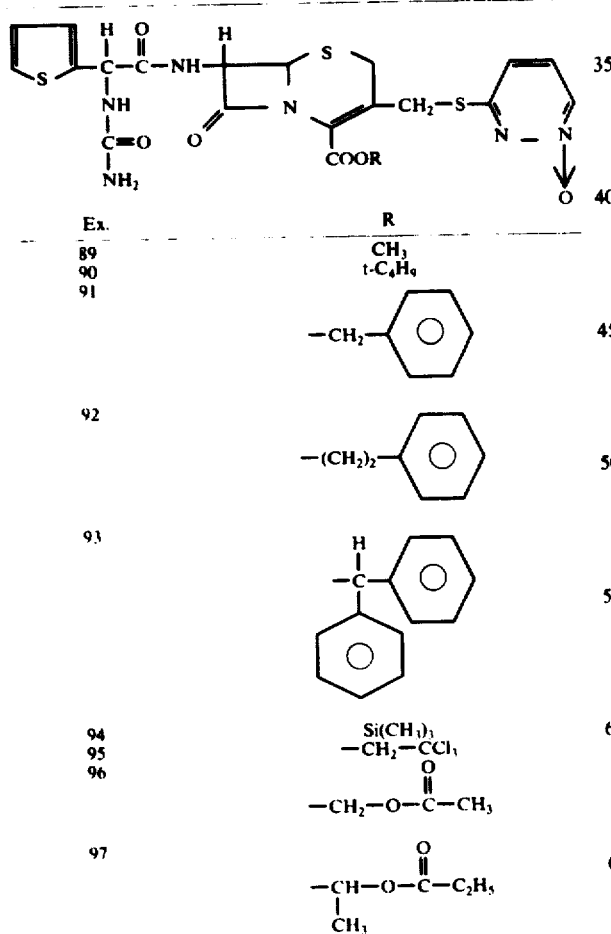

Similarly, the compounds of examples 3–88 can also be obtained in the various ester and salt forms shown in examples 89–106.

What is claimed is:

1. A compound of the formula wherein R is hydrogen, lower alkyl, phenyl-lower alkyl, diphenyl-lower alkyl, tri(lower alkyl)silyl, trihaloethyl, a salt forming ion, or $$-CH-O-C-R_6;$$
   $|$   $\|$
   $R_5$   $O$ $R_1$ is phenyl, phenyl-lower alkyl, substituted phenyl, or substituted phenyl-lower alkyl wherein said substituent is one to three members selected from the group consisting of halogen, lower alkyl, lower alkoxy, and hydroxy; $R_2$ is hydrogen or lower alkyl; $R_4$ is hydrogen, halogen, lower alkyl of 1 to 4 carbons, or lower alkoxy of 1 to 4 carbons; $R_5$ is hydrogen or lower alkyl; and $R_6$ is lower alkyl, phenyl, or phenyl-lower alkyl.

2. The compound of claim 1 wherein R is hydrogen, lower alkyl of 1 to 4 carbons, benzyl, phenethyl, diphenylmethyl, trimethylsilyl, 2,2,2-trichloroethyl, aluminum, an alkali metal, an alkaline earth metal, an amine salt, or

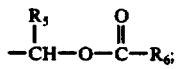

$R_1$ is phenyl, benzyl, phenethyl, or substituted phenyl, benzyl, or phenethyl wherein said substituent is one to three members selected from the group consisting of halogen, lower alkyl of 1 to 4 carbons, lower alkoxy of 1 to 4 carbons, and hydroxy; $R_2$ is hydrogen or lower alkyl of 1 to 4 carbons; $R_5$ is hydrogen or lower alkyl of 1 to 4 carbons; and $R_6$ is lower alkyl of 1 to 4 carbons, phenyl, benzyl, or phenethyl.

3. The compound of claim 2 wherein $R_2$ is hydrogen.
4. The compound of claim 3 wherein $R_4$ is hydrogen.
5. The compound of claim 2 wherein $R_2$ is lower alkyl of 1–4 carbons.
6. The compound of claim 5 wherein $R_4$ is hydrogen.
7. The compound of claim 4 wherein $R_1$ is phenyl, benzyl, phenethyl, substituted phenyl, benzyl or phenethyl wherein said substituent is one to three members selected from the group consisting of chlorine, bromine, methyl, methoxy, and hydroxy.
8. The compound of claim 7 wherein $R_1$ is phenyl or phenyl having a chloro, bromo, methyl, methoxy, or hydroxy substituent.
9. The compound of claim 8 wherein R is hydrogen and $R_1$ is phenyl.
10. The compound of claim 6 wherein $R_1$ is phenyl, benzyl, phenethyl, substituted phenyl, benzyl or phenethyl wherein said substituent is one to three members selected from the group consisting of chlorine, bromine, methyl, methoxy, and hydroxy.
11. The compound of claim 10 wherein $R_1$ is phenyl or phenyl having a chloro, bromo, methyl, methoxy, or hydroxy substituent, 2-.
12. The compound of claim 11 wherein R is hydrogen; $R_1$ is phenyl; and $R_2$ is methyl.

* * * * *